United States Patent
Itoh et al.

(10) Patent No.: US 7,398,685 B2
(45) Date of Patent: Jul. 15, 2008

(54) MEASURING METHOD USING SURFACE ACOUSTIC WAVE DEVICE, AND SURFACE ACOUSTIC WAVE DEVICE AND BIOSENSOR DEVICE

(75) Inventors: Atsushi Itoh, Kanagawa (JP); Motoko Ichihashi, Kanagawa (JP)

(73) Assignee: Ulvac, Inc., Chigasaki-Shi (JP)

( * ) Notice: Subject to any disclaimer, the term of this patent is extended or adjusted under 35 U.S.C. 154(b) by 207 days.

(21) Appl. No.: 11/149,530

(22) Filed: Jun. 10, 2005

(65) Prior Publication Data
US 2005/0277111 A1 Dec. 15, 2005

(30) Foreign Application Priority Data

Jun. 11, 2004 (JP) ............................. 2004-173925
Jun. 11, 2004 (JP) ............................. 2004-173926

(51) Int. Cl.
*G01N 11/16* (2006.01)
(52) U.S. Cl. ........................ 73/599; 73/579; 73/54.41; 73/61.49; 73/61.79
(58) Field of Classification Search ................... 73/579, 73/61.79, 61.49, 24.06, 54.41, 599
See application file for complete search history.

(56) References Cited

U.S. PATENT DOCUMENTS

| | | | | |
|---|---|---|---|---|
| 5,639,423 | A | * | 6/1997 | Northrup et al. ............... 422/50 |
| 5,674,742 | A | | 10/1997 | Northrup et al. ......... 435/286.5 |
| 5,852,229 | A | | 12/1998 | Josse et al. ................. 73/24.06 |
| 6,304,021 | B1 | | 10/2001 | Wolf et al. ................... 310/313 |
| 2004/0244466 | A1 | * | 12/2004 | Shen ........................... 73/24.01 |

(Continued)

FOREIGN PATENT DOCUMENTS

JP 06-050974 2/1994

(Continued)

OTHER PUBLICATIONS

Kondoh et al. "Simultaneous Detection of Density and Viscosity Using Surface Acoustic Wave Liquid-Phase Sensors", 2001, The Japan Society of Applied Physics.*

(Continued)

*Primary Examiner*—Hezron E. Williams
*Assistant Examiner*—Nashmiya S Fayyaz
(74) *Attorney, Agent, or Firm*—Kratz, Quintos & Hanson, LLP (57) ABSTRACT

A measuring method using a surface acoustic wave device, with which even in a case where a target substance having a different viscosity is added to a buffer liquid on the surface acoustic wave device it is possible to measure a mass load accurately without suffering an effect of this viscous load, and it is also possible to shorten the time taken for the temperature of the buffer liquid to stabilize and thereby shorten the time taken for the measurement. The measuring method provided is a method for exciting a surface acoustic wave on a substrate and measuring a property of a target substance placed on a detecting part on the substrate on the basis of a change in a characteristic of the surface acoustic wave, with the characterizing feature that a viscous load of the target substance is evaluated on the basis of fluctuations of at least two different frequencies among frequencies of the surface acoustic wave excited on the substrate, and a mass load of the target substance is measured by being separated from this viscous load.

12 Claims, 5 Drawing Sheets

U.S. PATENT DOCUMENTS

2007/0052516 A1 * 3/2007 Hines et al. .................. 338/34

FOREIGN PATENT DOCUMENTS

JP 2004-325257 11/2004

OTHER PUBLICATIONS

Diethelm Johannsmann, "Einsatz von Quarz-Resonatoren und Ellipsometrie zur visko-elastichen Charakterisierung von dunnen Schichten und Adsorbaten;" Dissertation, Fachbereich Physik, Universitat Mainz, Aug. 14, 1991 pp. 22-46.
European Search Report dated Oct. 13, 2005.

* cited by examiner

RAYLEIGH WAVE

Fig. 8(B)

SH WAVE (LOVE WAVE, ETC.)

MEASURING METHOD USING SURFACE ACOUSTIC WAVE DEVICE, AND SURFACE ACOUSTIC WAVE DEVICE AND BIOSENSOR DEVICE

BACKGROUND OF THE INVENTION

This invention relates to a method for exciting a surface acoustic wave on a substrate and measuring a property of a target substance placed on a detection part on the substrate on the basis of change in a characteristic of the surface acoustic wave.

As a method for measuring interactions of biological substances such as DNA and proteins, and for measurements using antigen-antibody reactions, surface acoustic wave devices are being used (see for example JP-A-06-133759 and "A Love wave sensor for (bio)chemical sensing in liquids" Sensors and Actuators A, 43(1994)38-43).

In this measurement using a surface acoustic wave device, either the center frequency $f_0$ of an acoustic wave excited in the device (the point at which the conductance of the measuring system is maximal or the point at which the phase is 0) is measured continuously or the center frequency $f_0$ is measured continuously using a network analyser or the like, and the mass load of the surface acoustic wave device is measured on the basis of fluctuation of this center frequency $f_0$.

Now, when a target substance is placed on the detection part of a surface acoustic wave device for measurement, besides the mass load, a viscous load caused by changes in viscosity affects the center frequency $f_0$, and it has not been possible to distinguish these loads clearly. When an attempt is made to investigate interactions of biological materials such as DNA and proteins or to investigate antigen-antibody reactions on the basis of frequency fluctuations with this kind of measurement system, because the viscosity of the target substance introduced into the measurement system and the viscosity of a buffer liquid used (a biochemical buffer liquid having NaCL or KCl or the like as a main constituent) often differ, it has not been possible to distinguish whether the measured frequency fluctuation is a result of mass load caused by bonding of DNA/proteins or bonding of antigen-antibodies or a result of viscous load, and it has not been possible to make precise measurements. And also because of liquid viscosity changes accompanying liquid temperature changes caused by room temperature changes and the introduction of target substances, sometimes precise measurements have not been possible.

SUMMARY OF THE INVENTION

It is therefore an object of the present invention to provide a measurement method with which even when a target substance having a different viscosity is added to a buffer liquid on a surface acoustic wave device it is possible to measure a mass load precisely without suffering an influence of this viscous load and to shorten the time taken for the temperature of the buffer liquid to stabilize and thereby shorten the time taken for the measurement.

As a result of assiduous research carried out to solve the problems explained above, the present inventors discovered a means of solving the problems by exciting a surface acoustic wave on a substrate, evaluating a viscous load of the object of detection on the basis of fluctuations of at least two different frequencies among frequencies of the surface acoustic wave excited, and removing the viscous load from the load acting on the surface acoustic wave device.

That is, a first aspect of the invention provides a method for exciting a surface acoustic wave on a substrate and measuring a property of a target substance placed on a detection part on the substrate on the basis of change of a characteristic of the surface acoustic wave, characterized in that a viscous load of the target substance is evaluated on the basis of fluctuations of at least two different frequencies among the frequencies of the surface acoustic wave excited on the substrate, and a mass load of the target substance is measured by being separated from this viscous load.

And, further effective solving means was made on the basis of the principles explained next.

1) First, a relationship between the viscous load and the mass load of an SH wave on a surface acoustic wave device will be explained.

The relationship between the propagation constant disturbance expression $\alpha + j\beta$ of an SH wave and the surface impedance $Z$ is as shown in the following expression Exp. 1. In the formula, $\alpha$ is an attenuation constant, $\beta$ is an actual propagation constant, and $S$ is the sensitivity of the device.

$$\frac{\Delta\alpha}{\beta} + j\frac{\Delta\beta}{\beta} = -SZ \qquad \text{Exp. 1}$$

The surface impedance $Z$ associated with viscous load in a Newton liquid with an SH wave is as given by the following expression Exp. 2. In the formula, $\omega$ is angular velocity, $\eta$ is the viscosity of the liquid, and $\rho$ is the density of the liquid.

$$Z = -\sqrt{\frac{\omega\eta\rho}{2}} - j\sqrt{\frac{\omega\eta\rho}{2}} \qquad \text{Exp. 2}$$

From the relationships of Exp. 1 and Exp. 2 it is possible to derive the relationships shown in the following expression Exp. 3.

$$\frac{\Delta\alpha}{\beta} = \frac{\Delta\beta}{\beta} = S\sqrt{\frac{\omega\eta\rho}{2}} \qquad \text{Exp. 3}$$

The surface impedance $Z$ associated with mass load is as shown by the following expression Exp. 4. In the formula, $m$ is the added mass and $A$ is the area of the detection part.

$$Z = -j\omega\frac{m}{A} \qquad \text{Exp. 4}$$

From the above expressions Exp. 1, Exp. 3 and Exp. 4 it is possible to derive the relationship shown in Exp. 5.

$$\frac{\Delta\beta}{\beta} = S\omega\left(\frac{m}{A}\right) \qquad \text{Exp. 5}$$

$$\frac{\Delta\alpha}{\beta} = 0$$

2) Next, an equivalent circuit of a surface acoustic wave device will be described.

Figure 1:
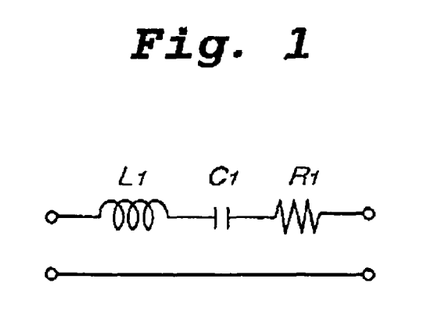
FIG. 1 is a view illustrating an equivalent circuit of a 2-port surface acoustic wave device.

An equivalent circuit of a 2-port surface acoustic wave device is shown in FIG. 1.

Figure 2:
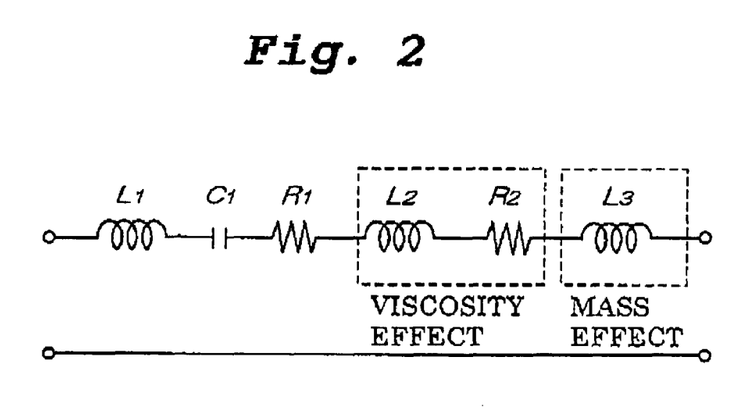
FIG. 2 is a view illustrating an equivalent circuit of when a viscous load and a mass load act on the equivalent circuit of FIG. 1.

The equivalent circuit when a viscous load and a mass load are added to this is shown in FIG. 2.

Here, the correspondence between the surface impedance Z and the parameters of the equivalent circuit is, in the case of viscous load from 1) above, as given by the following expression Exp. 6.

$$\frac{\Delta\alpha}{\beta} + j\frac{\Delta\beta}{\beta} = -SZ = -S'(R_2 + j\omega L_2) \qquad \text{Exp. 6}$$

In Exp. 6, S' is a value relating the surface impedance Z and the motional resistance $R_2$, motional inductances $L_2$, $L_3$ and is given by Exp. 7. $v_g$ is the group velocity of the wave and v is the sonic velocity of the wave.

$$S' = \frac{1}{\omega}\left(\frac{v}{v_g}\right)\frac{1}{2L_1} \qquad \text{Exp. 7}$$

From Exp. 6 above it is possible to derive the relationships shown in the following expressions Exp. 8 and Exp. 9.

$$R_2 = \frac{S}{S'}\sqrt{\frac{\omega\eta\rho}{2}} \qquad \text{Exp. 8}$$

$$L_2 = \frac{S}{S'}\sqrt{\frac{\eta\rho}{2\omega}} \qquad \text{Exp. 9}$$

On the other hand, the mass load can be expressed using the following formula Exp. 10.

$$j\frac{\Delta\beta}{\beta} = -SZ = -S'(j\omega L_3) \qquad \text{Exp. 10}$$

Therefore, by substituting Exp. 4 into Exp. 10, it is possible to derive the relationship shown in Exp. 11.

$$L_3 = \frac{S}{S'} \cdot \frac{m}{\omega A} \qquad \text{Exp. 11}$$

3) Next, the center frequency $f_0$ of a surface acoustic wave device will be discussed.

Figure 3:
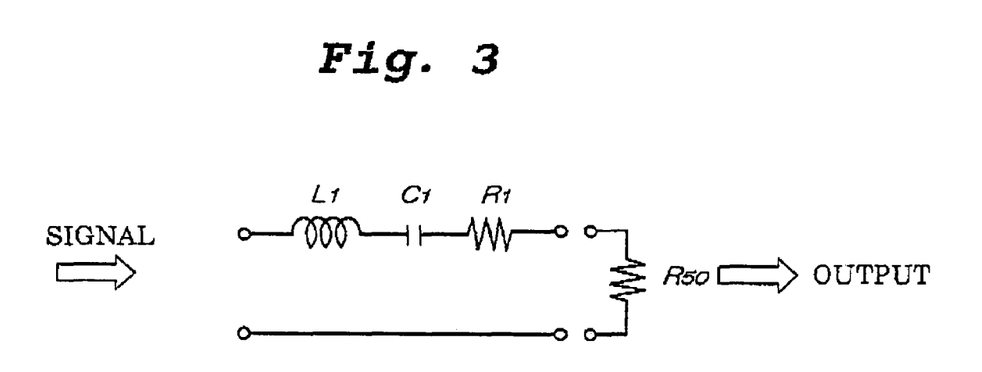
FIG. 3 is an operating view of the same circuit.

The transmission characteristic H(ω) of the equivalent circuit with no viscous load or mass load shown in FIG. 1, when measured with a measurement system (FIG. 3) of impedance 50Ω ($R_{50}$) using a network analyser or the like, is given by the following expression Exp. 12.

$$H(\omega) = \frac{R_{50}}{(R_{50} + R_1) + j\omega L_1 + \frac{1}{j\omega C_1}} \qquad \text{Exp. 12}$$

The real component (conductance G) of this is given by the following expression Exp. 13.

$$G = \text{Real}(H(\omega)) = \frac{R_{50}(R_{50} + R_1)}{(R_{50} + R_1)^2 + \left(\omega L_1 - \frac{1}{\omega C_1}\right)^2} \qquad \text{Exp. 13}$$

In this Exp. 13, the conductance G takes a maximum value when $\omega L_1 = 1/\omega C_1$. The center frequency $f_0$ at this time is given by the following expression Exp. 14.

$$f_0 = \frac{\omega_0}{2\pi} = \frac{1}{2\pi\sqrt{L_1 \cdot C_1}} \qquad \text{Exp. 14}$$

And the maximum value $G_{MAX}$ of the conductance G is given by the following expression Exp. 15.

$$G_{\max} = \text{Real}(H(\omega_0)) = \frac{R_{50}}{R_{50} + R_1} \simeq \frac{R_{50}}{R_1} \qquad \text{Exp. 15}$$

In the denominator of the final fraction in Exp. 15, $R_{50}$ is ignored because it is much smaller than $R_1$. This can be seen for example from the fact that in a 125 MHz Love wave device, when pure water is placed on the detection part, $R_1$ takes an extremely large value of about 16 kΩ.

Next, for the center frequency change $\Delta f_0$ when there are a viscous load and a mass load, because $L_1$ becomes $L_1+L_2+L_3$ and $C_1$ does not change, the following expression Exp. 16 is obtained.

$$\begin{aligned}\Delta f_0 &= \frac{1}{2\pi\sqrt{(L_1+L_2+L_3)\cdot C_1}} - \frac{1}{2\pi\sqrt{L_1 \cdot C_1}} \\ &\simeq \frac{1}{2\pi\sqrt{L_1 \cdot C_1}}\left(1 - \frac{L_2+L_3}{2L_1}\right) - \frac{1}{2\pi\sqrt{L_1 \cdot C_1}}\end{aligned} \qquad \text{Exp. 16}$$

(because $L_1$, $L_3$ take much smaller values than $L_1$)

$$= -\frac{1}{2\pi\sqrt{L_1 \cdot C_1}}\left(\frac{L_2+L_3}{2L_1}\right)$$

$$= -f_0\left(\frac{L_2+L_3}{2L_1}\right)$$

Therefore, the ratio of $\Delta f_0$ to $f_0$ is as given by the following expression Exp. 17.

$$\frac{\Delta f_0}{f_0} = -\frac{L_2}{2L_1} - \frac{L_3}{2L_1} \qquad \text{Exp. 17}$$

The first term in Exp. 17 is the viscous load and the second term is the mass load. In the viscous load, because from 2) there is the relationship $L_2=R_2/\omega$, the first term in Exp. 17 can be rewritten as shown by the following expression Exp. 18.

$$-\frac{L_2}{2L_1} = -\frac{R_2}{2\omega L_1} \qquad \text{Exp. 18}$$

Therefore, the viscous load $\Delta f_0$ is as given by the following expression Exp. 19.

$$\Delta f_0 \text{ (viscous load)} = -f_0 \cdot \frac{R_2}{2\omega L_1} \quad \text{Exp. 19}$$

$$\simeq -\frac{R_2}{4\pi L_1}$$

(from $\omega \simeq 2\pi f_0$)

From this, the center frequency change $\Delta f_0$ is as shown by the following expression Exp. 20.

$$\Delta f_0 = \Delta f_0 \text{ (viscous load)} + \Delta f_0 \text{ (mass load)} \quad \text{Exp. 20}$$

$$\simeq -\frac{R_2}{4\pi L_1} + \Delta f_0 \text{ (mass load)}$$

4) Finally, separation of the viscous load and the mass load will be explained.

When a viscous load and a mass load are present, $\omega_1$ and $\omega_2$ giving a value of half of the maximum value $G_{MAX}$ of the conductance G are obtained as shown by the following expression Exp. 21. In the formula, $R_1'=R_1+R_2$ and $L_1'=L_1+L_2+L_3$.

$$\text{Real}(H(\omega)) = \frac{R_{50}(R_{50} + R_1')}{(R_{50} + R_1')^2 + \left(\omega L_1' - \frac{1}{\omega C_1}\right)^2} \quad \text{Exp. 21}$$

$$= \frac{R_{50}}{2R_1'}$$

Because in this Exp. 21 $R_{50}$ is much smaller than $R_1'$ and can be ignored, Exp. 21 can be rewritten as shown by the following expression Exp. 22.

$$\frac{R_1'}{R_1'^2 + \left(\omega L_1' - \frac{1}{\omega C_1}\right)^2} = \frac{1}{2R_1'} \quad \text{Exp. 22}$$

The $\omega$ that satisfy this Exp. 22 are $\omega_1$ (Exp. 23) and $\omega_2$ (Exp. 24) ($\omega_1 < \omega_2$).

$$\omega_1 = \frac{1}{2} \cdot \frac{-R_1'C_1 + \sqrt{R_1'^2 C_1^2 + 4L_1'C_1}}{L_1'C_1} \quad \text{Exp. 23}$$

$$\omega_2 = \frac{1}{2} \cdot \frac{R_1'C_1 + \sqrt{R_1'^2 C_1^2 + 4L_1'C_1}}{L_1'C_1} \quad \text{Exp. 24}$$

Expressing Exp. 23 and Exp. 24 as $f_1$, $f_2$ ($f_1 < f_2$) yields the following expressions Exp. 25 and Exp. 26.

$$f_1 = \frac{\omega_1}{2\pi} \quad \text{Exp. 25}$$

$$= \frac{1}{4\pi} \cdot \frac{-R_1'C_1 + \sqrt{R_1'^2 C_1^2 + 4L_1'C_1}}{L_1'C_1}$$

$$= -\frac{R_1'}{4\pi L_1'} + \frac{\sqrt{R_1'^2 C_1^2 + 4L_1'C_1}}{4\pi L_1'C_1}$$

-continued $$f_2 = \frac{\omega_2}{2\pi} \quad \text{Exp. 26}$$

$$= \frac{1}{4\pi} \cdot \frac{R_1'C_1 + \sqrt{R_1'^2 C_1^2 + 4L_1'C_1}}{L_1'C_1}$$

$$= \frac{R_1'}{4\pi L_1'} + \frac{\sqrt{R_1'^2 C_1^2 + 4L_1'C_1}}{4\pi L_1'C_1}$$

Here, because the actual measured values of the equivalent circuit parameters when pure water is placed on a 125 MHz Love wave device as an example of an SH wave surface acoustic wave device are approximately $C_1'=5.4\times10^{-7}$F, $L_1'=3.0\times10^{-2}$H, $R_1'=1.6\times10^4\Omega$, the terms $R_1'^2$, $C_1'^2$ in Exp. 25 and Exp. 26 are small enough compared to $4L_1'C_1$, yielding the following expressions Exp. 27 and Exp. 28.

$$f_1 = -\frac{R_1'}{4\pi L_1'} + \frac{\sqrt{4L_1'C_1}}{4\pi L_1'C_1} \quad \text{Exp. 27}$$

$$f_2 = \frac{R_1'}{4\pi L_1'} + \frac{\sqrt{4L_1'C_1}}{4\pi L_1'C_1} \quad \text{Exp. 28}$$

Because the second terms in Exp. 27 and Exp. 28 are equal to the center frequency $f_0'$ when there are a viscous load and a mass load, $f_1$ and $f_2$ become as given by the following expressions Exp. 29 and Exp. 30.

$$f_1 = -\frac{R_1'}{4\pi L_1'} + f_0' \quad \text{Exp. 29}$$

$$f_2 = \frac{R_1'}{4\pi L_1'} + f_0' \quad \text{Exp. 30}$$

Here, substituting $L_1'=L_1+L_2+L_3$ and $R_1'=R_2+R_3$ and obtaining changes $\Delta f_1$ and $\Delta f_2$ in $f_1$, $f_2$ caused by viscous load and mass load, the following expressions Exp. 31 and Exp. 32 are obtained. In the formulas, $\Delta f_0=f_0'-f_0$ and it is assumed that $L_2$ and $L_3$ are extremely small compared to $L_1$.

$$\Delta f_1 \simeq -\frac{R_2}{4\pi L_1} + \frac{(R_1+R_2)(L_2+L_3)}{4\pi L_1^2} + \Delta f_0 \quad \text{Exp. 31}$$

$$\Delta f_2 \simeq \frac{R_2}{4\pi L_1} + \frac{(R_1+R_2)(L_2+L_3)}{4\pi L_1^2} + \Delta f_0 \quad \text{Exp. 32}$$

Here, because $$\Delta f_0 = -f_0\left(\frac{L_2+L_3}{2L_1}\right) \quad \text{Exp. 33}$$

Exp. 31 and Exp. 32 become as shown by the following expressions Exp. 34 and Exp. 35.

$$\Delta f_1 = -\frac{R_2}{4\pi L_1} + \Delta f_0\left(1 - \frac{R_1+R_2}{8\pi L_1 f_0}\right) \quad \text{Exp. 34}$$

-continued $$\Delta f_2 = \frac{R_2}{4\pi L_1} + \Delta f_0 \left(1 - \frac{R_1 + R_2}{8\pi L_1 f_0}\right) \quad \text{Exp. 35}$$

In these expressions Exp. 34 and Exp. 35, the term shown in the following expression Exp. 36 is small enough, at 1.6× $10^{-4}$.

$$\frac{R_1 + R_2}{8\pi L_1 f_0} \quad \text{Exp. 36}$$

Therefore, Exp. 34 and Exp. 35 can be rewritten as the following expressions Exp. 37 and Exp. 38.

$$\Delta f_1 = -\frac{R_2}{4\pi L_1} + \Delta f_0 \quad \text{Exp. 37}$$

$$\Delta f_2 = \frac{R_2}{4\pi L_1} + \Delta f_0 \quad \text{Exp. 38}$$

Here, when the $\Delta f_0$ of when there are a viscous load and a mass load obtained in 3) is substituted, Exp. 37 and Exp. 38 become as shown by the following expressions Exp. 39 and Exp. 40.

$$\Delta f_1 = -\frac{R_2}{2\pi L1} + \Delta f_0 (\text{mass load}) \quad \text{Exp. 39}$$

$$\Delta f_2 \mathbf{32} \, \Delta f_0 \, (\text{mass load}) \quad \text{Exp. 40}$$

Thus it can be seen that $\Delta f_2$ is the mass load only.
Also, from the following expression Exp. 41, $$\Delta f_1 - \Delta f_2 = -\frac{R_2}{2\pi L1} + \quad \text{Exp. 41}$$
$$\Delta f_0 (\text{mass load})1 - \Delta f_0 (\text{mass load})$$
$$= -\frac{R_2}{2\pi L1}$$

it can be seen that the following expression Exp. 42 is the viscous load only.

$$\frac{\Delta f_1 - \Delta f_2}{2} \quad \text{Exp. 42}$$

From the above, by using not the center frequency $f_0$ of the surface acoustic wave device but rather the two frequencies $f_1$, $f_2$ at ½ of the maximum value of the conductance G, separate measurement of the mass load and the viscous load, which could not be distinguished with measurement of the center frequency $f_0$ only, becomes possible.

Accordingly, as further effective solving means, a second aspect of the invention provides a measurement method according to the first aspect described earlier, characterized in that the two different frequencies are first and second frequencies $f_1$, $f_2$ ($f_1 < f_2$) that give a conductance of half of the conductance of the measuring system that gives the center frequency $f_0$ of the surface acoustic wave device.

And for these two frequencies $f_1$ and $f_2$ it is also possible to substitute frequencies of surface acoustic waves at which the phase is respectively shifted −45° and +45° with respect to a surface acoustic wave at the center frequency $f_0$.

Accordingly, a third aspect of the invention provides a measuring method according to the first aspect, characterized in that the two different frequencies are first and second frequencies $f_1$, $f_2$ ($f_1 < f_2$) at which the phase is shifted ±45° with respect to the center frequency $f_0$ excited on the substrate.

A fourth aspect of the invention provides a measuring method according to the second aspect or the third aspect, characterized in that the viscous load is evaluated on the basis of fluctuation in the difference between the first and second frequencies $f_1$, $f_2$.

A fifth aspect of the invention provides a measuring method according to any one of the first through third aspects, characterized in that the mass load is measured on the basis of fluctuation of a second frequency $f_2$ that is a frequency near to the center frequency $f_0$ and larger than the center frequency $f_0$.

A sixth aspect of the invention provides a measuring method according to any one of the first through third aspects, characterized in that the surface acoustic wave device is a Love wave device, an SH-SAW device, an STW device or an SH-APM device.

A seventh aspect of the invention provides a measuring method according to any one of the first through third aspects, characterized in that a solution and a target substance are agitated during measurement by a longitudinal surface acoustic wave being excited on the detection part.

An eighth aspect of the invention provides a surface acoustic wave device for carrying out a measuring method according to the seventh aspect, characterized in that it has a detection part on a substrate and is provided with a longitudinal wave excitation part on the substrate for exciting a longitudinal surface acoustic wave on the detection part.

A ninth aspect of the invention provides a surface acoustic wave device according to the eighth aspect, characterized in that the longitudinal wave excitation part and a transverse wave excitation part for exciting a transverse wave are the same part.

A tenth aspect of the invention provides a surface acoustic wave device according to the eighth aspect, characterized in that the longitudinal wave excitation part is disposed in a direction intersecting orthogonally with the direction of a transverse wave.

An eleventh aspect of the invention provides a surface acoustic wave device according to the eighth aspect, characterized in that the longitudinal wave is a Rayleigh wave or a modified Rayleigh wave.

A twelfth aspect of the invention provides a surface acoustic wave device according to the eighth aspect, characterized in that the substrate is made of ST-cut quartz, $LiTaO_3$, $LiNbO_3$, $Li_2B_4O_7$, $La_3Ga_5SiO_{14}$ or $KNbO_3$.

A thirteenth aspect of the invention provides a surface acoustic wave device according to the eighth aspect, characterized in that on the substrate, as the detection part, is formed a solid film layer for giving rise to a surface acoustic wave slower than the substrate surface would, and on that is further formed a metal film for fixing.

And a fourteenth aspect of the invention provides a biosensor device characterized in that it includes a surface acoustic wave device according to any one of the eighth through thirteenth aspects.

As described above, in the present invention, a surface acoustic wave is excited on a substrate, and a property of a target substance placed on a detection part on the substrate is measured on the basis of a change in a characteristic of the surface acoustic wave. The measuring method of the invention will now be described more specifically.

In the invention, a surface acoustic wave is produced for example on a piezoelectric substrate by an IDT with combined comblike electrodes, and a mass load is measured by measuring over a predetermined frequency range including the center frequency of the surface acoustic wave. The predetermined frequency range may be any range over which it is possible to measure fluctuation of the acoustic wave speed, but considering the effects of noise and so on it is desirable for the frequencies in the vicinity of the center frequency $f_0$ of the surface acoustic wave device to be made the range.

In this frequency range, at least two different frequencies are decided upon. Here, for the purposes of illustration two frequencies $f_a$ and $f_b$ will be used in the following description. Because these frequencies will exhibit different fluctuations with respect to the same viscous load, a ratio of viscous loads of the frequencies $f_a$, $f_b$ can be determined. And on the basis of this ratio of viscous loads, the viscous load on the surface acoustic wave device can be determined during measurement. As a result, by measuring the overall load acting on the surface acoustic wave device by for example by measuring fluctuation of $f_a$, determining the viscous load from the relationship between $f_a$ and $f_b$, and subtracting the viscous load from the overall load, it is possible to separate and measure the mass load and the viscous load. Processing such as the computation for evaluating the viscous load can be carried out either after the measurement or during the measurement.

In the measurement described above, in this invention highly accurate measurement is made possible by measurement being carried out using the center frequency $f_0$ of the surface acoustic wave device and specified frequencies $f_1$, $f_2$ that will be discussed below. Next, methods for acquiring these $f_1$ and $f_2$ will be described.

Figure 4:
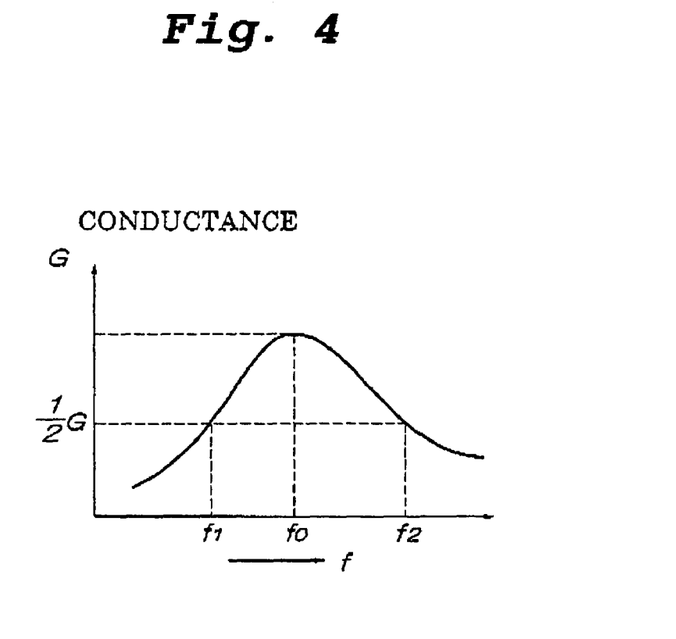
FIG. 4 is a graph showing a relationship between the frequency of a signal and the conductance of a surface acoustic wave device.

First, a surface acoustic wave is excited on the substrate, and the relationship between frequency and conductance G is measured in a predetermined frequency band including the center frequency $f_0$, as shown in FIG. 4. Then, from the figure, the frequencies giving the value of ½ of the conductance G, i.e. the frequencies $f_1$ and $f_2$ ($f_1<f_2$) are obtained. At the center frequency $f_0$, the conductance G takes an extreme value. And because the extreme value of the conductance G is a maximum value, it can be easily seen that the frequency giving the measured maximum conductance $G_{MAX}$ is the center frequency $f_0$. And in this invention, when the wavelength of the surface acoustic wave determined by the IDT pitch is written λ and the surface acoustic wave velocity is given by v, the frequency expressed $f_0=v/λ$ is made the center frequency $f_0$.

Next, when a buffer liquid is dripped onto the detection part of the surface acoustic wave device as necessary and a sample solution including a characteristic component constituting a target substance is introduced there, fluctuations arise in the frequencies $f_0$, $f_1$, and $f_2$. And if from the start of measurement until the end these frequencies $f_1$, and $f_2$ are recorded at predetermined time intervals and the fluctuation of $f_2$ is taken as change based on mass load and the fluctuation of $f_2-f_1$ is taken as change based on viscous load, then on the basis of these values it is possible to separate and measure a mass load and a viscous load. Addition to these mass and viscous loads the concentration of the target substance in the buffer liquid can be determined.

Although in the foregoing description $f_1$ and $f_2$ were obtained by scanning a predetermined frequency band, $f_1$ and $f_2$ can also be replaced with the following substitutes. That is, the measuring method of the invention can alternatively be carried out by exciting on a surface acoustic wave device only a surface acoustic wave having these frequencies $f_1$ and $f_2$.

1) The two frequencies at which the phase is +45° and −45° with respect to the center frequency $f_0$ are made $f_1$ and $f_2$.
2) Frequencies at which the insertion loss of when a signal from outside is applied to the surface acoustic wave device has fallen by a predetermined value from its maximum value are made $f_1$ and $f_2$. The predetermined value is not particularly limited, but for example may be 3 dB.
3) Two frequencies at which δB/δω, the susceptance B differentiated with respect to the angular velocity ω, is 0 are made $f_1$ and $f_2$.
4) A pair of quadrant frequencies on a circle drawn by a measurement point G+jB on an admittance plane of a Smith chart are made $f_1$ and $f_2$.

Next, a device used as a surface acoustic wave device in the invention will be described.

This surface acoustic wave device may be one of any structure such that it can excite a transverse surface acoustic wave on a substrate and on the basis of a frequency or the like changed by a target substance placed on a detection part of the substrate detect a property such as a mass load or a viscous load of the target substance. Consequently, the substrate of the surface acoustic wave device is not particularly limited either, and may for example be a piezoelectric substrate or one made by providing a piezoelectric membrane on an insulating substrate, and for example a Love wave device, an SH-SAW device, an STW device, or an SH-APM device can be used.

A Love wave device is a device with an IDT provided on the surface of a substrate of ST-cut quartz or the like and a material (e.g. $SiO_2$ or a polymer) having a lower speed than the transverse wave propagation speed of the substrate provided on the substrate surface in layer form, in which a surface wave (Love wave) with a transverse wave component perpendicular to the wave propagation direction of the wave and parallel to the substrate surface can be excited.

An SH-SAW device is a device with an IDT provided on $LiTaO_3$ (36° rotation Y plate X propagation, X-cut 150° propagation) or the like, in which a surface wave (piezoelectric surface sliding wave or the like) with a transverse wave component perpendicular to the wave propagation direction and parallel to the substrate surface can be excited.

An STW device is a device with an IDT grating on an AT-cut quartz substrate or the like, in which an SSBW (surface skimming bulk wave) propagating on the substrate is trapped on the substrate surface by the grating and a surface transverse wave is excited.

And an SH-APM device is a device with an IDT on an ST-cut quartz substrate or the like in which a plate wave propagating along the substrate surface and parallel to the substrate is excited.

Preferably, a longitudinal wave excitation part is provided on the substrate of the surface acoustic wave device described above.

This is to make it possible to agitate a target substance placed on the detection part and a solution such as buffer liquid or a liquid target substance by means of longitudinal waves.

This longitudinal wave excitation part may be disposed so as to intersect with the propagation direction of the transverse wave, or a transverse wave excitation part for exciting the transverse wave may be used for both. When it is disposed intersecting, because agitation can be carried out with the longitudinal wave while measurement is carried out with the transverse wave, accurate measurement is possible in a short measurement time. When on the other hand the transverse wave excitation part is used for both, the construction of the excitation part on the surface acoustic wave device is simplified. In this case, it is necessary for the longitudinal wave and the transverse wave to be produced using time-division.

The position in which the longitudinal wave excitation part is located is not particularly limited and can be anywhere on the substrate, but it is preferable for the longitudinal wave excitation part to be disposed in a direction intersecting orthogonally with the direction of the transverse wave at the detection part. This is because when a plurality of detection parts are disposed on the substrate, it enables longitudinal waves to be propagated to adjacent detection parts with a single longitudinal wave excitation part. And it is also because when as a piezoelectric substrate an ST-cut quartz is used, when the transverse wave excitation part is disposed in the Y-axis direction, the longitudinal wave excitation part is positioned in the X-axis direction and the amplitude of the longitudinal wave is maximal, and consequently a maximal agitating effect of the longitudinal waves can be obtained.

In the invention, a transverse surface acoustic wave is a surface wave with a transverse wave component perpendicular to the wave propagation direction and parallel to the substrate surface, and for example is a Love wave, an SSBW, a BGSW, an STW or an LSAW.

And a longitudinal surface acoustic wave is a wave having forward direction and depth direction displacement components, and for example is a Rayleigh wave or a modified Rayleigh wave in a layer structure.

A biosensor device according to the invention has a surface acoustic wave device described above. A device constituting a biosensor device may be any device having, as in related art, at least an oscillator capable of exciting in the surface acoustic wave device a transverse wave for detection, an analyzer device capable of measuring the frequency or the like of the transverse wave, and an oscillator capable of exciting a longitudinal wave. It is also possible for the same oscillator to be used for both the longitudinal wave and the transverse wave. And as the analyzing device it is also possible to use a network analyzer or an impedance analyzer with an oscillator for exciting the transverse wave integrated therewith.

DETAILED DESCRIPTION OF THE PREFERRED EMBODIMENTS

A preferred embodiment of the invention will now be described on the basis of the drawings.

Figure 5:
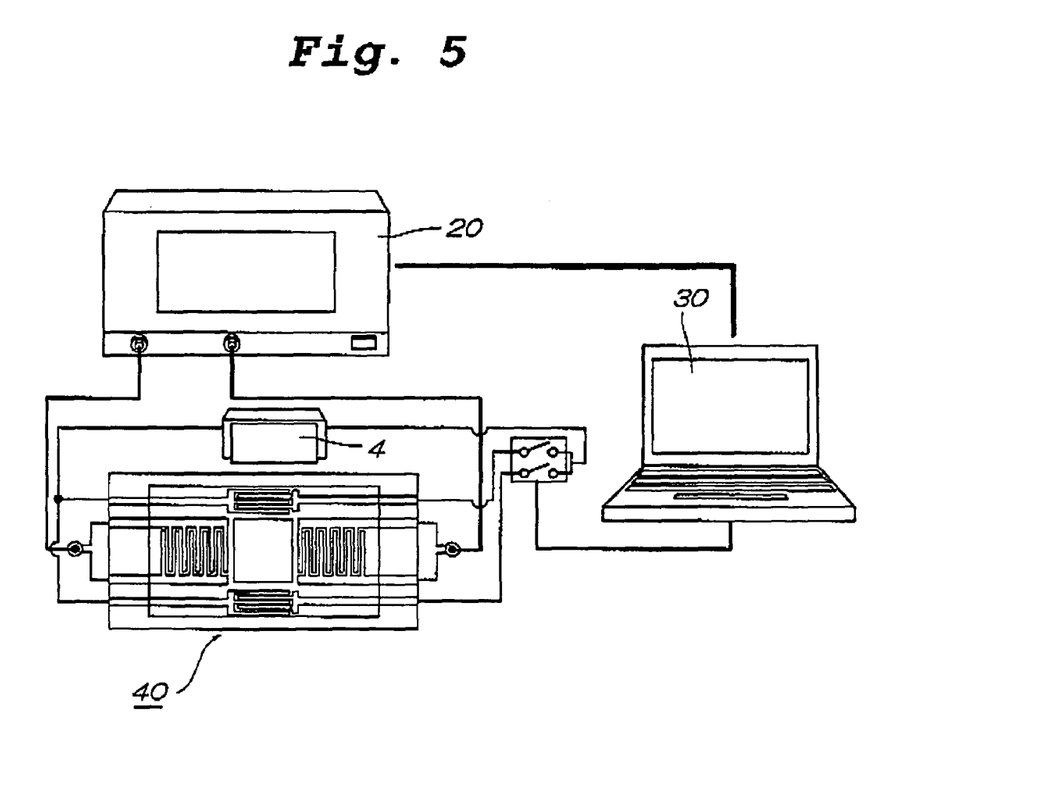
FIG. 5 is a view showing an example of a measuring apparatus of a preferred embodiment according to the invention.
Figure 6A:
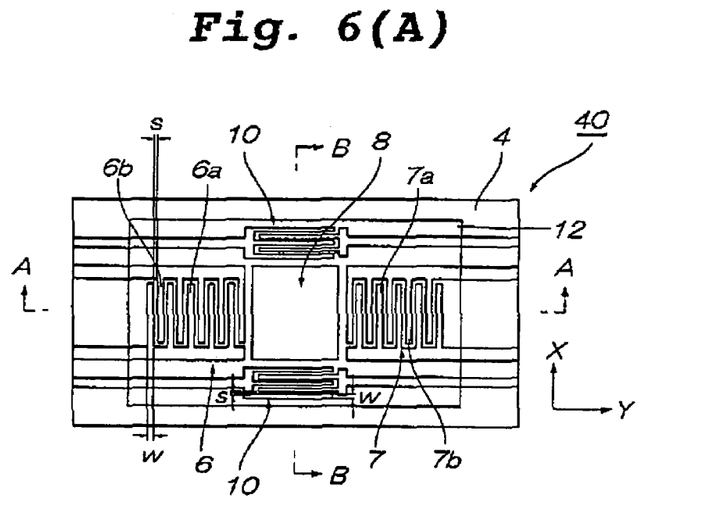
FIGS. 6A through 6C are views showing a preferred embodiment of a surface acoustic wave device according to the invention.
Figure 6B:
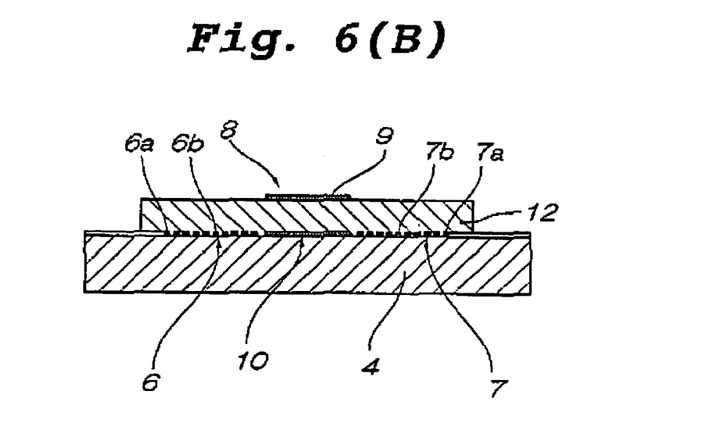
Figure 6C:
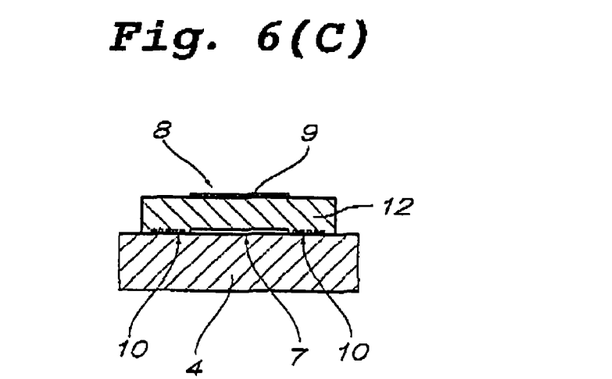

In FIG. 5, a surface acoustic wave device shown with the reference number 40 is connected to an analyzer 20, and the analyzer 20 can output a required a.c. signal to the surface acoustic wave device 40 and measure the conductance G of the surface acoustic wave device 40. A control unit 30 controls the operation of the analyzer 20; it varies the frequency of the signal that the analyzer 20 outputs to the surface acoustic wave device 40, and stores measurement results in correspondence with frequencies along with computation results. The analyzer 20 is an instrument sold as a network analyzer or an impedance analyzer or the like. The control unit 30 is also connected to longitudinal wave excitation part 10 (FIGS. 6A to 6C) of the surface acoustic wave device 40 via an oscillator shown with the reference number 4 in the figures, and controls these longitudinal wave excitation parts 10. The oscillator 4 generates a signal for exciting a Rayleigh wave, and in this preferred embodiment an oscillator that produces a 20 dBm signal at the frequency 80 MHz is used.

The surface acoustic wave device 40 is made by forming a thickness 0.5 mm, 33°30' rotation quartz ST-cut wafer 5 into a plate shape as shown in FIG. 3 to make a piezoelectric substrate 4, and providing on this a transverse wave excitation part 6, a receiving part 7 for converting transverse wave changes into an electrical signal, and a detecting part 8 formed on the surface of an acoustic wave propagation path between the transverse wave excitation part 6 and the receiving part 7.

Because the transverse wave excitation part 6 is for exciting a transverse wave for measurement, it is formed in a Y-axis direction of the ST-cut wafer. This transverse wave excitation part 6 is made up of 75 pairs of comblike electrodes 6a, 6b, and as shown in sectional view in FIG. 6B these comblike electrodes 6a, 6b are formed by layering on the piezoelectric substrate 4 a chrome film of thickness 50 nm and an Au film of thickness 150 nm in turn by sputtering and then using photolithography to remove unnecessary parts of the metal films by dry etching. The width w and the spacing s of the comblike electrodes 6a, 6b are each formed to 10 μm, and the wavelength λ (λ=2(w+s) ) of the surface acoustic wave excited is 40 μm. The receiving part 7 is also formed in the same way as the transverse wave excitation part 6.

In this preferred embodiment, besides the transverse wave excitation part 6 described above for exciting a transverse wave, longitudinal wave excitation parts 10, 10 for agitating a sample solution on the detecting part 8 are provided in an X-axis direction of the ST-cut wafer on opposite sides of the detecting part 8. The longitudinal wave excitation parts 10 are each made up of 50 pairs of comblike electrodes 10a, 10b made of the same material as the transverse wave excitation part 6 and the receiving part 7, and the width w and the spacing s of the electrodes 10a, 10b are each formed to 10 μm so that the wavelength λ of the surface acoustic wave excited is 40 μm.

A guide layer 12 consisting of an $SiO_2$ film of thickness about 3 μm is formed over the entire area of the piezoelectric substrate 4 with the transverse wave excitation part 6, the receiving part 7 and the longitudinal wave excitation parts 10, 10 formed on it, and on this guide layer 12 between the transverse wave excitation part 6 and the receiving part 7 are layered in turn a chrome film of thickness 20 nm and an Au film of thickness 100 nm to form a fixing film 9 constituting the detecting part 8. In this preferred embodiment, around the periphery of the detecting part 8, that is, on the guide layer 12 where the detecting part 8 is not present, siloxane is adhered as a result of evaporation of siloxane arising when a silicone adhesive hardens. Consequently, a water-repelling effect is obtained, and it is made possible for buffer liquid and liquid target substance and the like to be prevented from spreading beyond the detecting part 8.

By means of the construction described above, in the surface acoustic wave device 40, a 125 MHz Love wave is excited in the Y-axis direction of the piezoelectric substrate 4 and an 80 MHz Rayleigh wave is excited in the X-axis direction.

Next, an example of a method for making measurements with a biosensor device of the construction described above will be explained.

First, 150 µl of pure water is placed on the detecting part 8 of the surface acoustic wave device 40, and from the output side of the analyzer 20 a 125 MHz a.c. signal being oscillated over a range of 1 MHz is inputted to the transverse wave excitation part 6 to excite a transverse wave on the surface of the piezoelectric substrate 4.

From this state, when a target substance is added to the detecting part 8, the speed of the Love wave excited by the transverse wave excitation part 6 fluctuates, this fluctuation is converted into an electrical signal by the transverse wave receiving part 7 and inputted to the input side of the analyzer 20 and measured every 1 second, and changes in frequency or the like are stored in the analyzer 20.

A specific example of measurement using this construction will now be described.

First, 150 µl of pure water is placed on the detecting part 8 of the surface acoustic wave device 40.

After 60 seconds from the measurement start time, 1 µl of avidin (concentration 70 µg/ml), constituting a first sample, was introduced; after 700 seconds 2 µl of a mixture of concentration 30% glycerol and avidin (the avidin concentration being the same as above), constituting a second sample, was introduced; and after 1400 seconds 1 µl of concentration 30% glycerol constituting a third sample was introduced. During this measurement period, by the analyzer 20 every 1 second a 1 MHz frequency band was swept, the center frequency $f_0$ of the surface acoustic wave device 40 was stored and a maximum value of the conductance G in the vicinity of the center frequency $f_0$ was obtained, a first frequency $f_1$ and a second frequency $f_2(f_1<f_2)$ at which this conductance G was at ½ of its maximum value were obtained, and these values $f_0$, $f_1$ and $f_2$ were stored.

The avidin of the samples attaches to the detecting part 8 and applies a mass load, but the glycerol does not attach to the detecting part 8 and only applies a viscous load.

Figure 7:
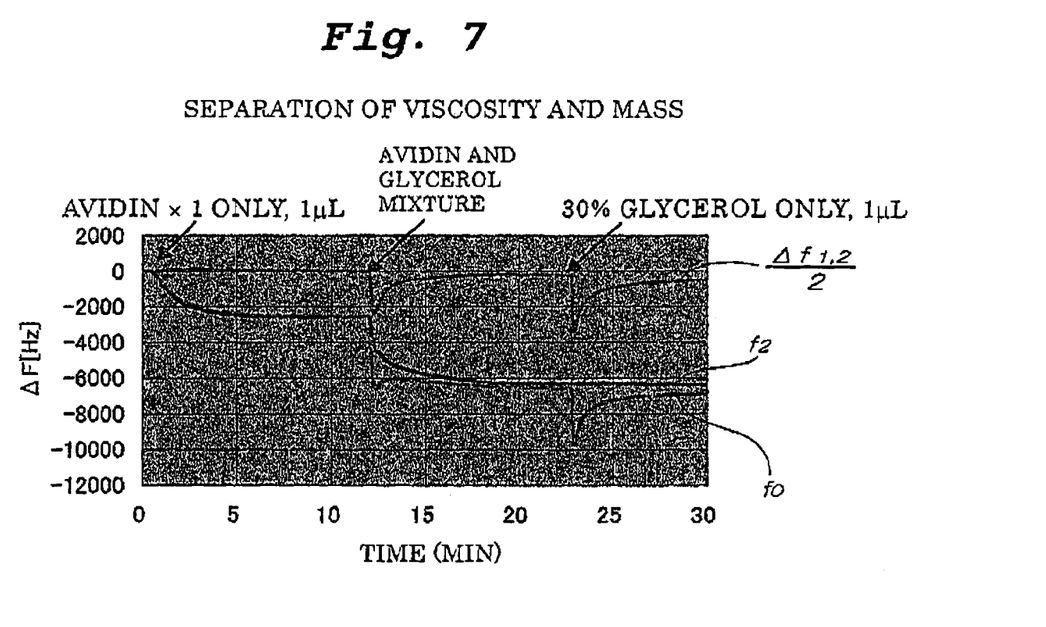
FIG. 7 is a graph for illustrating a relationship between mass load, viscous load and frequency fluctuation.

The $f_0$ and $f_2$ of the stored data and, in this preferred embodiment, $\Delta f_{1,2}/2$ ($\Delta f_{1,2}=f_2-f_1$) as a computed parameter based on the difference between $f_1$ and $f_2$, were plotted to obtain FIG. 7.

As is clear from FIG. 7, when the first sample is introduced, because the avidin attaches to the detecting part 8 of the surface acoustic wave device 40 and the mass load fluctuates, the $f_0$ and $f_2$ sensing this fluctuate by 2000 Hz. With respect to this, because $\Delta f_{1,2}/2$ does not suffer any influence of mass load it maintains a constant value.

Next, when the second sample is introduced, in addition to a mass load fluctuation, the center frequency $f_0$ undergoes a viscous load fluctuation caused by the detecting part settling as a result of the glycerol. Accordingly the frequency once decreases greatly to take time to be stabilized. With respect to this, it can be seen that $f_2$ does not undergo fluctuation due to the viscous load resulting from the glycerol, and decreases so that it clearly shows the fluctuation of the mass load, and compared to $f_0$ the time to it stabilizing is short. And, it can be seen that $\Delta f_{1,2}/2$ shows only the fluctuation of the viscous load caused by the glycerol.

Finally, when the third sample is introduced, in addition to a mass load fluctuation, the center frequency $f_0$ also undergoes a viscous load fluctuation caused by the glycerol, and it can be seen that it decreases greatly and then returns to what it was before. With respect to this, $f_2$ is not subject to the viscous load fluctuation caused by the glycerol, and maintains a constant value. And it can be seen that $\Delta f_{1,2}/2$ detects the viscous load fluctuation caused by the glycerol and the frequency decreases.

As can be seen from the measurements above, if $f_2$ is used to measure the mass load and $\Delta f_{1,2}/2$ is used to measure the viscous load, at the time of measurement it is possible to measure the mass load and the viscous load separately. Therefore, it is possible to evaluate the viscous load from the overall load acting on the surface acoustic wave device 40 and measure the mass load alone accurately.

In the preferred embodiment described above the measuring system is not limited, and it may alternatively be made a measuring system that can obtain $f_1$ and $f_2$ directly, without using the center frequency $f_0$.

And, in the preferred embodiment described above, to make the measurements more accurate, preferably, the measuring systems of the surface acoustic wave device 40 and the analyzer 20 are calibrated before the measurement.

Figure 8A:
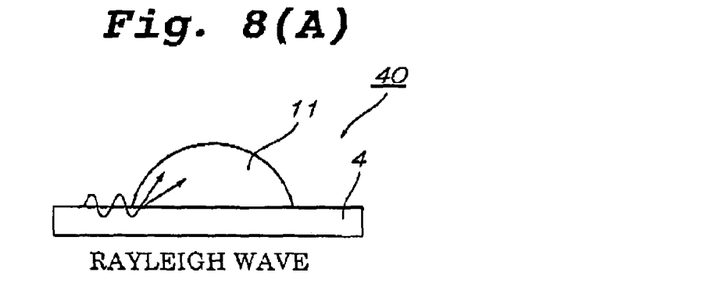
FIGS. 8A and 8B are views illustrating longitudinal and transverse waves during measurement with a surface acoustic wave device according to the invention.
Figure 8B:
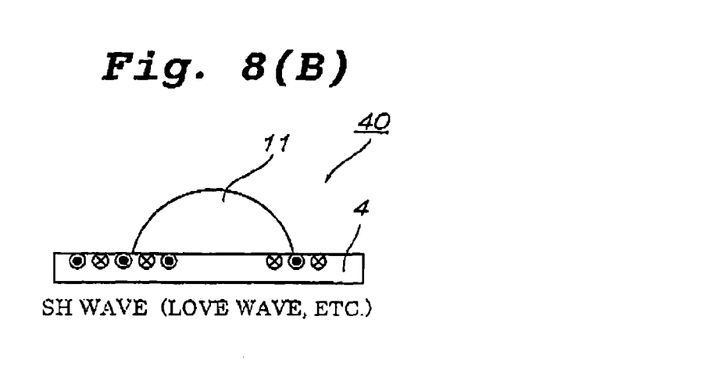

At the time of the measurement, when the longitudinal wave excitation parts 10, 10 are excited by the oscillator 4 on a command from the control unit 30, as shown in FIG. 8A, the interior of the liquid mixture 11 of the pure water and the target substance is agitated by the Rayleigh wave. At this time, the Love wave undergoes effects of the mass load and the viscous load of the target substance as shown in FIG. 8B.

Figure 9:
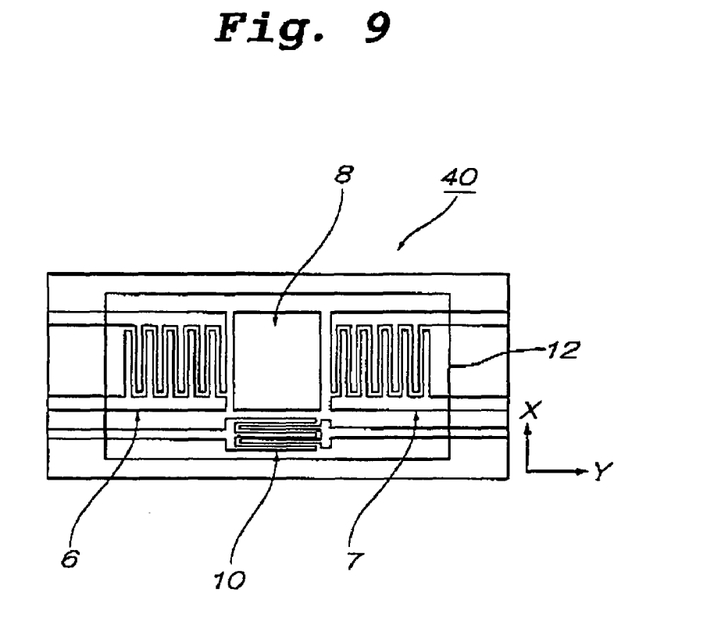
FIG. 9 is a view illustrating a variation of a surface acoustic wave device according to the invention.

Although in the foregoing preferred embodiment longitudinal wave excitation parts 10, 10 were disposed facing each other on both sides of the detecting part 8, as long as they can agitate the buffer liquid and liquid target substance on the detecting part 8 the disposition and number of longitudinal wave excitation parts 10 is not limited. Accordingly for example a longitudinal wave excitation part 10 may be disposed on one side of the detecting part 8 only, as shown in FIG. 9.

Figure 10A:
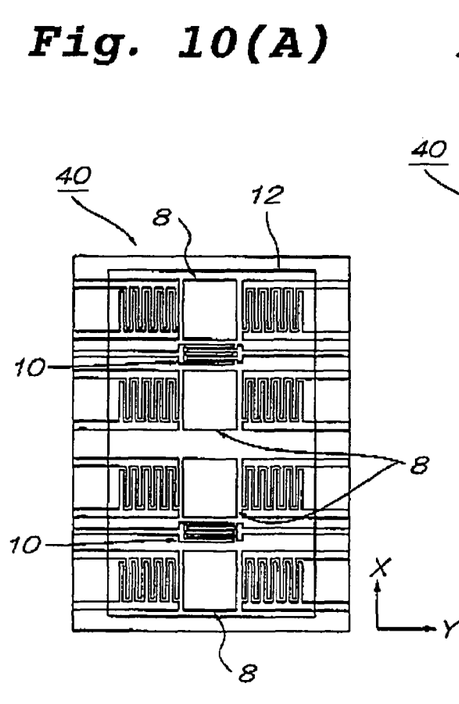
FIGS. 10A and 10B are views showing other variations of surface acoustic wave devices according to the invention.
Figure 10B:
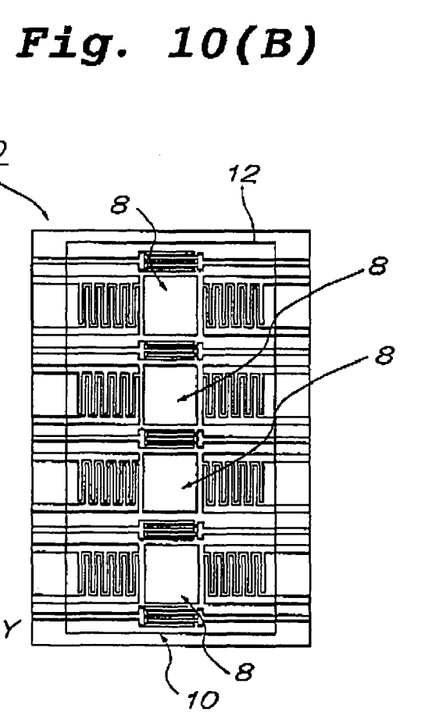

And, multiple detecting parts 8 may be provided, as shown in FIGS. 10A and 10B. In this case, just one excitation part 10 may be provided between adjacent detecting parts 8, 8 as shown in FIG. 10A, or excitation parts 10 may be provided on both sides of each detecting part 8, as shown in FIG. 10B.

With the measuring method of this invention it is possible to measure a mass load and a viscous load independently, even when a viscous load arises when the target substance is added during the measurement. Therefore, by evaluating this viscous load, it is possible to measure a mass load extremely accurately in a test of highly viscous blood or a test of bacilli included in a food product. And also when the viscosity changes because the temperature of the target substance added to the buffer liquid is different, the same applies. After a cell containing the buffer liquid is set on the device, the time to the temperature becoming constant can be shortened.

With this invention, by a longitudinal wave for agitation being excited on the surface acoustic wave device in addition to the transverse wave for measurement, because the mixture of a solution of buffer liquid or the like and a target substance placed on the detecting part, or a liquid target substance, can be agitated, it is possible to perform measurement of extremely small quantities of target substance accurately.

What is claimed is:

1. A measuring method for exciting a surface acoustic wave on a substrate and measuring a property of a target substance, comprising the steps of:
   placing the target substance on a detecting part on the substrate of a surface acoustic wave device;
   measuring a characteristic of the surface acoustic wave, at at least two different frequencies among frequencies of the surface acoustic wave excited on the substrate; which frequencies are first and second frequencies $f_1$, $f_2$ ($f_1<f_2$) giving a conductance of ½ the conductance of the surface acoustic wave device that gives the center frequency $f_0$ of the surface acoustic wave device;
   evaluating a viscous load of the target on the basis of fluctuations of the characteristic at the two different frequencies; and
   measuring a mass load of the target substance by separating the target substance from the viscous load.

2. A measuring method according to claim 1, wherein the two different frequencies are first and second frequencies $f_1$, $f_2$ ($f_1<f_2$) at which the phase is shifted by ±45° with respect to the center frequency $f_0$ of the surface acoustic wave device.

3. A measuring method according to claim 1 or 2, wherein the viscous load is evaluated on the basis of fluctuation of the difference between the first and second frequencies $f_1$, $f_2$.

4. A measuring method according to 2, wherein the mass load is measured on the basis of fluctuation of the second frequency $f_2$ that is near to the center frequency $f_0$ and larger than the center frequency $f_0$.

5. A measuring method according to claim 1 or 2, wherein the surface acoustic wave device is a Love wave device, art SH-SAW device, an STW device or an SH-APM device.

6. A measuring method according to claim 1 or 2, wherein the target substance in solution is agitated during measurement by longitudinal surface acoustic wave being excited on the detection part.

7. A measuring method according to claim 6, wherein there is a longitudinal wave excitation part provided on the substrate to excite a longitudinal surface acoustic wave on the detecting part.

8. A method according to claim 7, wherein the longitudinal wave excitation part can also excite a transverse wave.

9. A method according to claim 7, wherein the longitudinal wave excitation part is disposed in a direction orthogonal to the propagating direction of a transverse wave.

10. A method according to claim 7, wherein the longitudinal wave is a Rayleigh wave or a modified Rayleigh wave.

11. A method according to claim 7, wherein the substrate is made of ST-cut quartz, $LiTaO_3$, $LiNbO_3$, $Li_2B_4O_7$, $La_3Ga_5Si_1$, or $KNbO_3$.

12. A method according to claim 7, wherein on the substrate, a solid film layer for producing a surface acoustic wave slower than the substrate surface is formed in order to form the detecting part, and on the solid film layer a metal film for fixing is further layered.

* * * * *